(12) United States Patent
Moore et al.

(10) Patent No.: US 10,905,790 B1
(45) Date of Patent: Feb. 2, 2021

(54) SARS-COV-2 COMBINATION AIR PURIFIER AND DECONTAMINATION AND BIOBURDEN REDUCTION SYSTEM FOR SURGICAL MASKS/RESPIRATORS

(71) Applicants: Cullen Thomas Moore, Newtown, CT (US); Neha Varma Nadimpally, Hyderabad (IN)

(72) Inventors: Cullen Thomas Moore, Newtown, CT (US); Neha Varma Nadimpally, Hyderabad (IN)

( * ) Notice: Subject to any disclaimer, the term of this patent is extended or adjusted under 35 U.S.C. 154(b) by 0 days.

(21) Appl. No.: 16/935,495

(22) Filed: Jul. 22, 2020

(51) Int. Cl.
| | |
|---|---|
| *G01N 21/00* | (2006.01) |
| *G01N 23/00* | (2006.01) |
| *A61N 5/00* | (2006.01) |
| *A61L 9/20* | (2006.01) |
| *A61M 16/06* | (2006.01) |
| *A61M 16/10* | (2006.01) |
| *A61L 101/26* | (2006.01) |

(52) U.S. Cl.
CPC .............. *A61L 9/20* (2013.01); *A61M 16/06* (2013.01); *A61M 16/1065* (2014.02); *A61L 2101/26* (2020.08); *A61L 2209/12* (2013.01); *A61L 2209/14* (2013.01)

(58) Field of Classification Search
CPC ........ A61L 2/00; A61L 2/0029; A61L 2/0047; A61L 2/02; A61L 2/022; A61L 2/08; A61L 2/10
USPC ............... 422/24; 250/453.11, 455.11, 492.1
See application file for complete search history.

(56) References Cited

U.S. PATENT DOCUMENTS

| | | | | |
|---|---|---|---|---|
| 7,939,016 | B2 * | 5/2011 | Lu .............................. | A61L 2/20 422/22 |
| 2010/0119461 | A1 * | 5/2010 | Bicard-Benhamou ....................... | A61P 17/08 424/49 |
| 2013/0256560 | A1 * | 10/2013 | Yerby ....................... | A61L 2/10 250/455.11 |
| 2019/0063763 | A1 * | 2/2019 | Kleinberger ............ | A61L 2/022 |

OTHER PUBLICATIONS

This non-Patent Document was submitted in the IDS dated Aug. 25, 2020. Shin and Liu, Copper Foam Structures with Highly Porous Nanostructured Walls, Chem. Mater 2004, 16:5460-5464 (2004) (Year: 2004)*
Yu et al, entitled Catching and killing of airborne SARS-Cov-2 to control spread of COVID-19 by a Heated Air Disinfection System, published in Materials Today Physics, Jul. 7, 2020 (100249).
Shin and Liu, Copper Foam Structures with Highly Porous Nanostructured Walls, Chem. Mater 2004, 16:5460-5464 (2004).
Letter to Editor, Aerosol and Surface Stability of SARS-COV-2 as Compared to SARS-COV-1, N. Eng. J. Med. 2020: 382:1564-1657 (2020).

(Continued)

*Primary Examiner* — Monzer R Chorbaji
(74) *Attorney, Agent, or Firm* — Withers Worldwide

(57) ABSTRACT

The present invention in an embodiment relates generally to an air purifier having an ultraviolet wave chamber which is accessible from the exterior designed for the placement of masks/respirators in need of decontamination. Such device preferably makes use of filters comprising copper foam.

20 Claims, 1 Drawing Sheet

(56) References Cited

OTHER PUBLICATIONS

Lore et al., Effectiveness of Three Decontamination Treatments against Influenza Virus Applied to Filtering Facepiece Respirators, Ann Occup. Hyg.: Jan:56(1):92-101 (2012).

Lindsley et al., Effects of Ultriviolet Germicidal Irradiation (UVGI) on N95 Respirator Filtration Performance and Structural Integrity, J. Occup Environ Hyg.; 12(8): 509-17 (2015).

Fischer et al., Assessment of N95 respirator decontamination and re-use for SARS-CoV-2, medRxiv preprint, Apr. 24, 2020.

Buanno et al., Far-UVC light (222 nm) efficiently and safely inactivates airborne human coronaviruses, Scientific Reports, Nature Research:10:10285 (2020).

More heat than light for UVC LEDs, Electronics Weekly.com, Sep. 2017.

\* cited by examiner

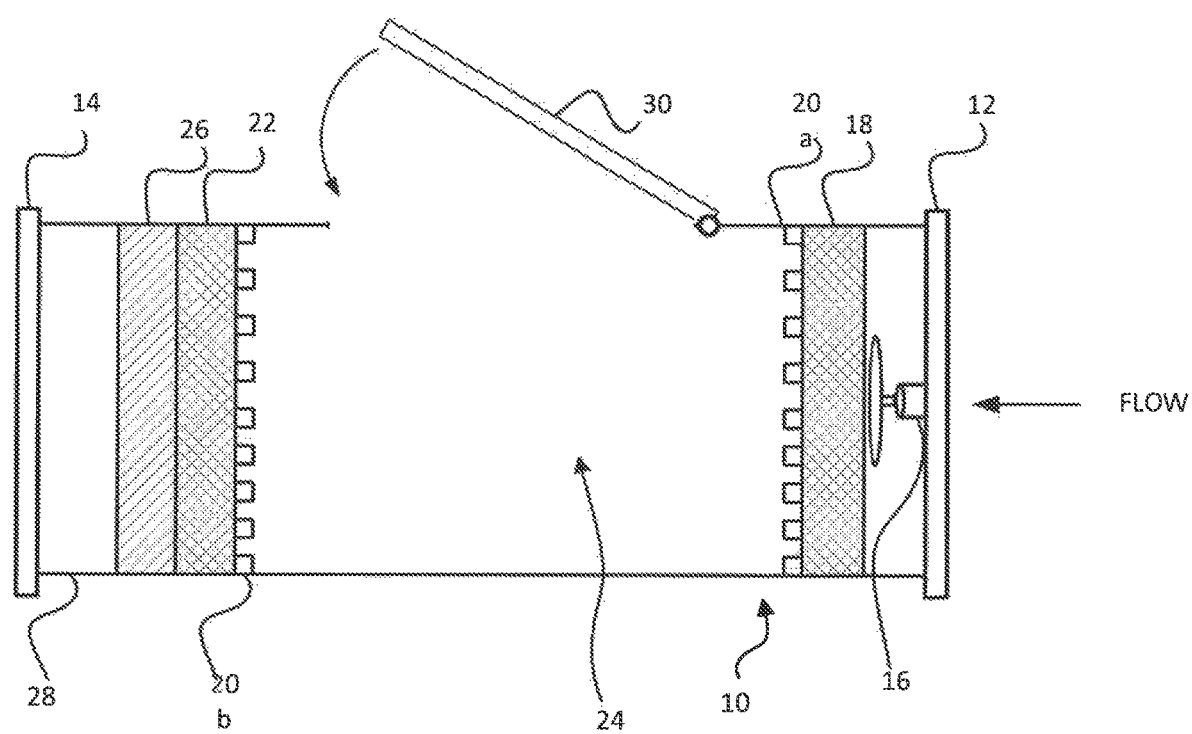

SARS-COV-2 COMBINATION AIR PURIFIER AND DECONTAMINATION AND BIOBURDEN REDUCTION SYSTEM FOR SURGICAL MASKS/RESPIRATORS

CROSS REFERENCE TO RELATED APPLICATIONS

The present application does not claim priority to any other pending patent application national or foreign.

TECHNICAL FIELD

The present invention in an embodiment relates generally to an air purifier having an ultraviolet wave chamber which is accessible from the exterior designed for the placement of masks and/or respirators in need of decontamination. In an embodiment, there is also provided an air purifier employing one or more copper foam filter (a filter comprising copper foam), and optionally one or more activated-carbon air filters, in conjunction with an ultraviolet wave chamber, to deactivate infectious viruses, such as coronaviruses (in particular SARS-CoV-2), found in the ambient air and configured to accept masks and/or respirators (to deactivate infectious viruses thereon). In particular there is provided a combination air purifier and surgical mask/respirator decontamination system, providing a mask/respirator storage unit in the air purification path wherein the masks/respirators/respirator are exposed both to the air flow through the purifier and to ultraviolet wave radiation.

BACKGROUND

Coronaviruses (CoV) are widespread viruses that cause a variety of illnesses ranging from the common cold to COVID-19. Coronaviruses are lipid-bilayer enveloped positive-sense, single-stranded RNA virus, and a member of the Coronaviridae family. Coronaviruses have club-shaped spikes that project from their substantial spherical surface.

A new coronavirus, designated SARS-CoV-2, has ravaged the world since 2019. This virus first jumped into humans in Wahun, Hubei Province, China, and then quickly spread across the world. COVID-19 represents a global public health concern and WHO has declared it a public health emergency. SARS-CoV-2 rapidly increased in spread in an epidemic scale since its first appearance in Wuhan, China, around December 2019. On Jan. 31, 2020, the Secretary of HHS issued a declaration of public health emergency related to COVID-19.

The FDA has recognized that decontamination reduction systems play an important role in the ongoing efforts to help address the shortages of surgical masks/respirators during COVID-19. In particular the FDA has recognized that the need for surgical masks/respirators may outpace the supply available to healthcare organizations during the COVID-19 public health emergency. It has also recognized that multiuse of surgical masks/respirators will dramatically decrease the bioburden associated with single-use masks. Therefore, the FDA has expressed interest in interacting with others about systems that may be effective at decontaminating or reducing the bioburden of otherwise single-use, disposable surgical masks/respirators.

As noted in the FDA's May 2020 Guidance for Industry and Food and Drug Administration Staff in "Recommendations for Sponsors Requesting EUAs for Decontamination and Bioburden Reduction Systems for Surgical Masks/Respirators During the Coronavirus Disease 2019 (COVID-19) Public Health Emergency," as of May 2020 there were no cleared or approved devices for decontamination or bioburden reduction of surgical masks/respirators. Therefore, the 510K process is not available to market systems intended to decontaminate or reduce the bioburden of surgical masks/respirators. Such devices must be cleared by a EUA submission.

In its Guidance, the FDA notes that the least resistant microorganisms to germicidal chemicals are lipid or medium-size viruses. Coronaviruses are lipid viruses. It is this recognition that has led to the inventors propose in one embodiment filtration of air using a highly-lipophilic filter, such as Ultra-X-Tex which has an apparent pore size of 100 microns.

Coronavirus particles are spherical in nature and have a diameter of approximately 0.125 microns, with the smallest particles being about 0.06 microns and the largest about 0.14 microns. From a filtration point of view, it is the droplet that must be removed from the air, and these range from 0.5 microns to approximately 15 microns, with most in the lower range. Presently only HEPA filters can filter out such viruses, with some filters capturing even nanoparticles (3 to 20 nanometers).

While HEPA filters may have pores small enough to capture such viruses, pore size is not the whole story in regard to whether a filter will effectively remove an infectious virus from a stream of air passing through it. Even HEPA filters cannot capture 0.01 percent of particles smaller than 5 nanometers. In an article by Yu et al, entitled *Catching and killing of airborne SARS-Cov-2 to control spread of COVID-19 by a Heated Air Disinfection System*, published in Materials Today Physics, Jul. 7, 2020 (100249), the authors found that Nickel foam traps SARS-COV-2 virus particles although the material is stated to have randomly located pores of 50-500 micrometers, that is substantially larger in size than the virus. By adding heat to the nickel foam (200° C.), the authors indicate that they were able to capture and kill nearly 99.8% of aerosolized SARS-CoV-2.

The present inventors have recognized that coronaviruses can be trapped and killed without the need to apply heat as in Yu et al., by instead using copper foam filters.

For thousands of years, long before people understood germs or viruses, copper was known to protect against disturbances in health. Indeed, an Egyptian doctor circa 1700 B.C. noted that cooper was known to protect health for at least a millennium before. The Phoenicians were known to apply bronze savings to their wounds to prevent infection. And in India, it has long been known that diarrhea can be prevented by drinking from a copper cup.

Copper is believed to kill due to its possession of a free electron in its outer orbital shell of electrons which allows it to take part in oxidation-reduction reactions. Copper ions are thought to blast a pathogen, punching holes in the viral coating and creating free radicals that cause damage. More so, it is believed to seek and destroy RNA inside a virus.

Copper foam typically is sold with a cell size of 200 micrometers to 600 micrometers. However, technique are known to get the surface pores down to from about 25 micrometers to 50 micrometers (See, Shin and Liu, *Copper Foam Structures with Highly Porous Nanostructured Walls*, Chem. Mater 2004, 16:5460-6464 (2004). The present inventors have recognized in that copper foams also have high and meandering surface areas, the odds of a virus particle coming into contact with the copper is very high. The present inventors were not dissuaded by recent studies that have shown the SARS-CoV-2 virus being infectious on copper surfaces for up to 4 hours (See, Letter to Editor,

*Aerosol and Surface Stability of SARS-COV-2 as Compared to SARS-COV-1*, N. Eng. J. Med. 2020: 382:1564-1567). Indeed, the inventors recognized that such studies employed static nebulized size contacts, and that dynamic air contact would cause the virus to be exposed to multiple copper atoms leading to a much quicker reduction in infectivity.

The present inventors have also recognized that copper foams are highly porous, with a relative density of around 37 percent, allowing for easy air flow through the same.

Besides copper, ultraviolet light is known to be viricidal. UVC light is known to possess a very powerful germicidal effect not only on bacteria, but also viruses. It is believed that such radiation leads to pyrimidine dimers interfering with DNA and RNA replication and transcription. Typically such UV C irradiation has been performed using low-pressure mercury UV lamps which emit about a 254 nm peak wavelength (86 percent of light at around 254 nm.)

Before COVID-19, studies had shown that ultraviolet germicidal irradiation was able to reduce virus load by greater than 4 log median a tissue culture infective dose placed on a N95 filtering face piece respirator ("FFR"). Such reduction was also seen in regard to microwave-generated steam, and moist heat. See. Lore et al., *Effectiveness of three decontamination treatments against influenza virus applied to filtering facepiece respirators*, Ann. Occup. Hyg. 2012: January: 56(1)92-101. Lindsley et al., *Effects of Ultriviolet Germicidal Irradiation (UVGI) on N95 Respirator Filtration Performance and Structural Integrity*, J. Occup Environ Hyg. 2015; 12(8): 509-17 also found in testing 4 N95 masks/respirators that UV sterilization might be used on such masks/respirators to allow for reuse. However using 120-950 $J/cm^2$, these authors found there was a reduction in the breaking strength of certain of the straps used on the N95 masks/respirators.

Studies conducted by Fischer et al., *Assessment of N95 respirator decontamination and re-use for SARS-CoV-2*, medRxiv preprint, Apr. 24, 2020, https://doi.org/10.1101/2020.04.11.20062018, demonstrate that UV radiation of 260-285 nm for about 50 minutes could be used to decontaminate surgical respirators of SARS-CoV-2 for re-use up to three times.

The present inventors have recognized that UV radiation the problem seen by Lindsley et al. in regard to the straps, could be reduced by using far-UVC light which requires much less energy for its veridical activity.

Recent research has shown that far-UVC light in the range of 207 to 222 nm can control the spread of airborne-mediated microbial disease without the need for more penetrating UVC wavelengths outside this range. See, Buanno et al., *Far-UVC light (222 nm) efficiently and safely inactivates airborne human coronaviruses*, Scientific Reports, Nature Research, 2020:10:10285. UVC light emitting diodes (LEDs) proffer further advantage over Mercury UV lamps in that they require no warm-up time for maximum intensity output. Far-UVC light can also effectively be generated by filtered excimer lamps which are known to emit UV-C light from 172 nm to 310 nm. Buonno et al. found in respect of the air alone it took approximately 25 minutes to inactivate 99.9 percent of human coronaviruses alpha HCV-229 E and beta HCoV-OC43, shorter than the time noted by Fischer et al. using higher wavelengths. The present inventors have understood that such lower UVC wavelengths of 207 to 222 nm can work as well on masks/respirators that might be infected with SARS-CoV-2.

LED arrays could be used to provide UVC wavelengths over abroad range, including 260 nm to 405 nm and now in the range of 207 to 222 nm. The employment of LEDS leads to considerable heat at the base of the bulb (See, *More heat than light for UVC LEDs*, Electronics Weekly.com, September 2017). Excimer lamps also produce heat. The present inventors recognized that copper foam is an excellent heat sink that could be used in conjunction with such UVC light sources to help dissipate heat. Further, by putting such light sources into the air flow of an air purifier, heat is further dissipated.

As noted by the FDA in its recommendations for sponsors requesting EUAs for Decontamination and Bioburden Reduction Systems for Surgical Masks/respirators, a number of factors need to be taken into account. One of these factors is to determine what are the protective measures for staff carrying out the decontamination or bioburden reduction in processing the masks/respirators. Until present, proposed masks/respirators decontamination systems have stood as stand-alone devices to which the previously used masks are transferred. The present inventors have recognized that such devices by design are remote to the site where the mask use occurred. They have recognized that this requires the masks to be carefully removed from the many locations where they were originally used, and then carefully transported to the remote standalone decontamination system and placed carefully therein. The inventors have recognized that such protocol leads to the ability of the virus to be disseminated from the site in which it is supposed to be of concern to areas of where concern is low.

The idea advanced by the present inventors of including a mask/respirator decontamination component in an air purifier overcomes the need to be moving possibly contaminated masks and respirators to a central decontamination device. In any case of virus suspicion, especially in patient rooms, it would be of advantage to have an air purifier that effectively removes infectious virus from the situs where the infection is feared. At the same time, it would be advantageous if the mask/respirator used in conjunction with a visit to a presumed infectious person to be decontaminated in the same location at a safe distance from the suspected virus source. The present invention allows for the same, in both decontaminating the ambient air at the patient situs from infectious virus, as well as decontaminating the mask/respirator used by the attending providers at such situs allowing for multiple use of masks/respirators while minimizing the potential of spread of virus.

SUMMARY OF THE INVENTION

Accordingly, the invention herein provides in an embodiment an air purifier having an ultraviolet wave chamber which is accessible from the exterior, which is internally configured for the placement of masks/respirators in need of decontamination (e.g., such as by having hooks within the chamber for hanging the masks/respirators (which hooks can be opposed to allow for fixed placement of the mask/respirator) or a wheel with attachment devices for holding the masks or respirators in a fixed position thereon). The invention also provides an air purifier employing one or more copper foam air filters (a filter comprising copper foam which may or may not be entirely copper foam), optionally having an activated carbon filter and/or HEPA filter, which is used to deactivate viruses, in particular infectious coronaviruses such as SARS-CoV-2, in the ambient air. Such copper foam filter(s) may be employed in conjunction with an ultraviolet wave chamber. In a preferred embodiment there is provided a combination air purifier and mask/respirator decontamination system, providing a mask/respirator storage unit in the air purification path wherein the masks/respirators are exposed both to the air flow through the purifier and ultraviolet wave radiation.

BRIEF DESCRIPTION OF DRAWINGS

FIG. 1 is an internal, cross sectional view of an air purifier and PPE decontamination unit according to the present invention looking from the top.

BRIEF DESCRIPTION OF SPECIFIC EMBODIMENTS

In one embodiment of the present invention is an air purifier with PPE decontamination comprising: (a) a housing having an inlet for receiving air, and an outlet for exhausting air, wherein the housing provides an air flow path for airflow between the inlet and outlet, (b) a fan disposed inside the housing adjacent to the air inlet; (c) a chamber in the air flow path having one or more ultraviolet light emitting sources in access therewith, said chamber having a sealable door allowing for access from outside the chamber; (d) a first air flow filter downstream from said air inlet but before said ultraviolet light chamber; (e) a second air flow filter upstream of said ultraviolet light chamber but downstream of said air outlet. In a preferred embodiment the ultraviolet light chamber is of sufficient size to allow for the placement of one or more masks and/or respirators therein. The ultraviolet light emitting source may be selected from at least one of a mercury lamp, an LED, and an excimer lamp. Preferably an ultraviolet light emitting source is a UVC emitting LED or an excimer lamp. More preferably the UVC emitting LED or excimer lamp produces wavelengths between about 207 to about 222 nm. The first and/or second airflow filter may be selected from at least one of copper foam and a lipophilic filter, such as Ultra-X-Tech (Ultratech International, Inc., Jacksonville, Fla.), and optionally combined with a replaceable activated carbon filter/bed or HEPA filter/bed. The chamber may have hooks in it on which to stretch masks, or may include a wheel upon which such masks are placed and stretched so as to keep each mask separate from the other. Such positions may be marked to allow one to understand where their particular mask is located versus that of other masks.

Another embodiment of the present invention is an air purifier comprising: (a) a housing having an inlet for receiving air, and an outlet for exhausting air, wherein the housing provides an air flow path for airflow between the inlet and outlet, (b) a fan disposed inside the case adjacent to the air inlet; (c) a first air flow filter downstream from said air inlet; (d) a second air flow filter upstream of said first air flow filter and downstream of said airflow outlet, wherein at least the first or second filter comprises copper foam. Such embodiment may further comprise a lipophilic filter, such as Ultra-X-Tech (Ultratech International, Inc., Jacksonville, Fla.), and/or a replaceable activated carbon filter/bed or HEPA filter/bed. In a preferred embodiment when there is a non-copper foam filter the filter is a HEPA filter, optionally with an activated carbon filter. In another preferred embodiment the other non-copper foam comprising filter is a lipophilic filter. In yet another preferred embodiment the air purifier comprises three or more filters of which one is a HEPA filter and one is a copper foam containing filter. Such air purifier may comprise in an embodiment additionally: (e) a chamber having one or more ultraviolet light emitting source in access therewith between the first air flow filter and the second air flow filter. If a chamber is included, the ultraviolet light emitting source may be selected from at least one of a mercury lamp, an LED, and an excimer lamp, preferably an ultraviolet light emitting source is a UVC emitting LED. More preferably the UVC emitting LED or excimer lamp produces wavelengths between about 207 to about 222 nm.

In another embodiment of the present invention is an air purifier comprising: (a) a housing having an inlet for receiving air, and an outlet for exhausting air, wherein the housing provides an air flow path for airflow between the inlet and outlet, (b) a fan disposed inside the case adjacent to the air inlet; (c) a chamber having one or more ultraviolet light emitting source in access therewith; (d) a first air flow filter downstream from said air inlet but before said ultraviolet light chamber; (e) a second air flow filter upstream of said ultraviolet light chamber but downstream of said air outlet; wherein at least the first or second filter comprises at least one of copper foam and a lipophilic filter. Such filters may be supplemented with a replaceable activated carbon filter/bed or HEPA filter/bed. In a preferred embodiment at least the first or second filter comprises copper foam. In another preferred embodiment at least one of the first and second filters is a lipophilic filter. In a more preferred embodiment at one of said first and second filters is a copper foam comprising filter, while the other filter is a lipophilic filter. In a more preferred embodiment, both the first and second filters are a copper foam filter. Optionally there is a third filter of activated carbon. The ultraviolet light emitting source may be selected from at least one of a mercury lamp, an LED, and an excimer lamp. Preferably an ultraviolet light emitting source is a UVC emitting LED or excimer lamp. More preferably the UVC emitting LED produces wavelengths between about 207 to about 222 nm.

In another embodiment of the present invention is an air purifier with a PPE decontamination capability comprising: (a) a housing having an inlet for receiving air, and an outlet for exhausting air, wherein the housing provides an air flow path for airflow between the inlet and outlet, (b) a fan disposed inside the housing adjacent to the air inlet; (c) one or more ultraviolet light emitting sources located in the air flow path; (d) a sealable door allowing for access into said housing an air flow path space proximal to said ultraviolet light emitting sources wherein said airflow path space is configured to permit one or more masks/respirators to be placed into said space separate from one another; (e) a first air flow filter downstream from said air inlet but before said ultraviolet light emitting sources; (f) a second air flow filter upstream of said ultraviolet light emitting sources but downstream of said air outlet. The ultraviolet light emitting source may be selected from at least one of a mercury lamp, an LED, and an excimer lamp. Preferably an ultraviolet light emitting source is a UVC emitting LED or excimer lamp. More preferably the UVC emitting LED or excimer lamp produces wavelengths between about 207 to about 222 nm. The first and/or second airflow filter may be selected from at least one of copper foam, a lipophilic filter, such as Ultra-X-Tech (Ultratech International, Inc., Jacksonville, Fla.), a HEPA filter and activated carbon filter.

In accord with the CDC strategies for optimizing the supply of facemask, Jun. 28, 2020, masks may be discarded if soiled, damaged, or hard to breathe through. Only masks and respirators that are in otherwise good condition may therefore be selected to be decontaminated.

Turning now to the drawing, there is shown an internal view of an embodiment air purifier with PPE decontamination capability looking from the top.

Combination air purifier and PPE decontamination device 24 is shown to be comprised of an inlet 12 for receiving air and an outlet 14 for exhausting air. Booster fan 16 is downstream from inlet 12. It may be coupled to a control system, as known in the art (not shown) to trigger booster fan 16 as needed to maintain a desired air flow rate, such as about 250 ft./min by means of a flow monitor (not shown). Booster fan 16 moves air through filter 18 which may be a filter comprised of copper foam. Booster fan moves air through filter 18 and into chamber 24 which is accessible externally via door 30. Door 30 is preferably attached to a kill switch that stop the movement of air and turns off ultraviolet LED arrays 20a and 20b (which may be replaced with UV generating mercury lamps or excimer lamps) that are located along chamber 24 providing any air coursing there through (the chamber) with ultraviolet decontamination rays. Preferably the LEDs (or light source) are set to produce UV radiation in the far Ultraviolet range of 207-222 nm range. Another filter 22 flanks the end of chamber 24 at the end proximal to outlet 14. Such filter may also be a filter comprising copper foam. When cooper foam comprises filter 18, ultraviolet LED arrays 20a and 20b (or other UV generating source) may be coupled thereto to permit the copper foam to act as a heat sink. Optional filter 26 may comprise a lipophilic filter designed to attach to lipophilic biological materials, such as the coating found in respect of coronaviruses. Downstream of the final filter 25 may include a HEPA filter 28 or other nanoparticle filtering filter. Additionally an atomizing humidifier or dehumidifier (not shown) may be added if need to maintain a comfortable ambient environment.

The invention claimed is:

1. A combination air purifier and mask and respirator decontamination device comprising:
   (a) a housing having an inlet for receiving air, and an outlet for exhausting air, wherein the housing provides an air flow path for airflow between the inlet and outlet,
   (b) a fan disposed adjacent to the air inlet;
   (c) a chamber in the air flow path configured to permit multiple surgical masks and respirators to be placed in the chamber so each is separate from one another and having labelling associated with each mask and respirator, and having one or more ultraviolet light emitting sources in access therewith, said chamber having a sealable door allowing for access from outside the chamber, said door coupled to a kill switch to stop airflow between the inlet and outlet and turn off the ultraviolet light emitting sources when the door to the chamber is opened;
   (d) a first air flow filter downstream from said air inlet but before said ultraviolet light chamber; and
   (e) a second air flow filter upstream of said ultraviolet light chamber but downstream of said air outlet.

2. The combination air purifier and mask and respirator decontamination device of claim 1 wherein the ultraviolet light emitting source is selected from at least one of a mercury lamp, an LED, and an excimer lamp.

3. The combination air purifier and mask and respirator decontamination device of claim 1 wherein the ultraviolet light emitting source is a UVC emitting LED and/or excimer lamp.

4. The combination air purifier and mask and respirator decontamination device of claim 3 wherein the UVC emitting LED or excimer lamp is limited to producing wavelengths between about 207 to about 222 nm.

5. The combination air purifier and mask and respirator decontamination device of claim 1 wherein at least one of the first and/or second airflow filters is selected from at least one of a copper foam filter and a lipophilic filter.

6. The combination air purifier and mask and respirator decontamination device of claim 1 wherein the first and/or second airflow filters comprise copper foam.

7. An air purifier comprising:
   (a) a housing having an inlet for receiving air, and an outlet for exhausting air, wherein the housing provides an air flow path for airflow between the inlet and outlet,
   (b) a fan disposed adjacent to the air inlet;
   (c) a first air flow filter downstream from said air inlet; and
   (d) a second air flow filter upstream of said first air flow filter but downstream of said air outlet;
   wherein at least the first or second filter comprises a copper foam containing filter.

8. The air purifier of claim: 7 further comprising: (e) a chamber having one or more ultraviolet light emitting source in access therewith between the first air flow filter and the second air flow filter.

9. The air purifier of claim 8 wherein the light emitting source is a UVC emitting LED and/or excimer lamp.

10. The air purifier of claim 9 wherein the UVC emitting LED or excimer lamp is limited to producing wavelengths between about 207 to about 222 nm.

11. The air purifier of claim 7 wherein the first filter is copper foam and the second filter is a lipophilic filter.

12. The air purifier of claim 7 wherein the first and second air filter are comprised of copper foam.

13. The air purifier of claim 12 wherein the copper foam is coupled to the LEDs and/or excimer lamps to act as a heat sink.

14. The air purifier of claim 7 wherein the copper foam has surface cores of from about 25 micrometers to 50 micrometers.

15. A combination air purifier and PPE decontamination device:
   (a) a housing having an inlet for receiving air, and an outlet for exhausting air, wherein the housing provides an air flow path for airflow between the inlet and outlet,
   (b) a fan disposed adjacent to the air inlet;
   (c) one or more ultraviolet light emitting sources located in the air flow path;
   (d) a sealable door allowing for access into said housing an air flow path space proximal to said ultraviolet light emitting sources configured to permit multiple surgical masks and respirators to be placed therein such that each is separate from one another and having labelling associated with each mask and respirator, said sealable door coupled to a kill switch to kill the fan disposed adjacent to the air inlet and turn off the ultraviolet light emitting sources when the door is opened;
   (e) a first air flow filter downstream from said air inlet but before said ultraviolet light emitting sources; and
   (f) a second air flow filter upstream of said ultraviolet light emitting sources but downstream of said air outlet
   wherein at least the first or second filter comprises a copper foam filter.

16. The combination air purifier and PPE decontamination device of claim 15 wherein the ultraviolet light emitting source is selected from at least one of a mercury lamp, an LED, and an excimer lamp.

17. The combination air purifier and PPE decontamination device of claim 16 wherein the light emitting source is a UVC emitting LED and/or excimer lamp limited to producing UV-C light in the range of between about 207 to about 222 nm.

18. The combination air purifier and PPE decontamination device of claim 17 further comprising a lipophilic filter.

19. The combination air purifier and PPE decontamination device of claim 18 wherein there is a third-airflow filter selected from a HEPA filter and an activated carbon filter.

20. The combination air purifier and PPE decontamination device of claim 19 wherein there is a fourth filter comprising at least one of: a HEPA filter and an activated carbon filter.

* * * * *